United States Patent [19]

Haughton

[11] Patent Number: 4,941,364
[45] Date of Patent: Jul. 17, 1990

[54] HOLDER FOR MOLTEN METAL SAMPLING DEVICE

[75] Inventor: Gary H. Haughton, Burlington, Canada

[73] Assignee: Evacuo Enterprises Limited, Hamilton, Canada

[21] Appl. No.: 406,529

[22] Filed: Sep. 13, 1989

Related U.S. Application Data

[63] Continuation-in-part of Ser. No. 240,506, Sep. 6, 1988.

[30] Foreign Application Priority Data

Sep. 9, 1987 [GB] United Kingdom ................ 8721185
May 5, 1989 [GB] United Kingdom ................ 8910406

[51] Int. Cl.$^5$ .............................................. G01N 1/12
[52] U.S. Cl. ............................ 73/864.53; 73/DIG. 9
[58] Field of Search .................... 73/864.51–864.59, 73/DIG. 9; 266/99

[56] References Cited

U.S. PATENT DOCUMENTS

| | | | |
|---|---|---|---|
| 3,452,602 | 7/1969 | Hackett | 73/DIG. 9 |
| 3,877,309 | 4/1975 | Hance | 73/DIG. 9 |
| 4,067,242 | 1/1978 | Judge | 73/DIG. 9 |
| 4,211,117 | 7/1980 | Cure | 73/DIG. 9 |

FOREIGN PATENT DOCUMENTS 1526144  4/1968  France ........................... 73/864.55

*Primary Examiner*—Robert Raevis
*Attorney, Agent, or Firm*—Shoemaker and Mattare, Ltd.

[57] ABSTRACT

A holder for a molten metal sampling device includes a pipe having a guidance chamber in a lower portion and a molten metal sampling device in an upper portion. The pipe is open downwardly and a closure element closes the opening. The closure element has a density such as to cause it to float upwardly in the molten metal being sampled. A protective cover, preferably of two parts, encloses the closure element and a lower portion of the pipe. A retaining device such as a spring clip holds the separate parts of the protective cover together around the closure element and the lower part of the pipe. The retaining device is adapted to fail upon contact with the molten metal, thus releasing the portions of the protective cover so that they will separate and float upwards, whereupon the closure element also separates and floats away, allowing molten metal into the guidance chamber and the sampling device.

8 Claims, 1 Drawing Sheet

HOLDER FOR MOLTEN METAL SAMPLING DEVICE

This is a continuation-in-part of U.S. patent application Ser. No. 240,506, filed on Sept. 6, 1988.

The present invention relates to molten metal sampling devices, especially to such devices with a non-diluting and non-contaminating protection cap and entrance system.

BACKGROUND OF THIS INVENTION

Prior samplers have been designed with capping and entrance system that melted along with and into the molten material being sampled. This caused a source of undesirable contaminants to flow into the actual sample chamber. The prior method also allowed elements contained in the capping system to cause a diluting effect on similar elements contained in the molten batch material.

The location being sampled may contain extremely low (typically, 10 to 50 ppm) values of certain elements, for example, C, S, Mn, $O_2$, H and N, that must be accurately analyzed in order to produce a high quality product. At these minute ranges, any outside contamination or dilution can cause a significant error in accurate analysis.

Patents representative of the prior art in this area are as follows:

U.S. Pat. No. 4,428,245, issued Jan. 31, 1984 to Nakamura et al;
U.S. Pat. No. 4,007,641, issued Feb. 15, 1977 to Kelsey;
U.S. Pat. No. 4,557,152, issued Dec. 10, 1985 to Plessers et al;
U.S. Pat. No. 4,646,578, issued Mar. 3, 1987 to Lawrenz et al;
U.S. Pat. No. 4,170,139, issued Oct. 9, 1979 to Narita et al;
U.S. Pat. No. 4,250,753, issued Feb. 17, 1981 to Collins;
U.S. Pat. No. 4,140,019, issued Feb. 20, 1979 to Falk;
U.S. Pat. No. 4,112,772, issued Sept. 12, 1978 to McDevitt;
U.S. Pat. No. 4,037,478, issued July 26, 1977 to Cure;
U.S. Pat. No. 4,002,073, issued Jan. 11, 1977 to Collins;
U.S. Pat. No. 3,332,288, issued July 24, 1967 to Mladenovich;
U.S. Pat. No. 3,693,449, issued Sept. 26, 1972 to Collins;
U.S. Pat. No. 4,051,732, issued Oct. 5, 1979 to Falk;
U.S. Pat. No. 3,859,857, issued Jan. 14, 1975 to Falk;

In my U.S. patent application Serial No. 240,506, entitled "Molten Metal Sampling Device", there is proposed a novel capping and entrance system that very much reduces contamination or dilution of the obtained sample. A cap is provided, which is rapidly released from the sampling device upon immersion in the molten metal, and simply floats away.

However, even with the improvement provided by my earlier invention, there remains a slight risk that small portions from the slag layer can be carried down to the region of the sampling device as the latter is plunged downwardly through the slag.

Accordingly, an object of one aspect of this invention is to further decrease the risk of contamination or dilution of an obtained sample.

In a general way, this object is achieved by providing an additional protective cover around the outside of the sampler, the additional protective cover being of a material which tends to repel slag components. The additional protective cover is a composite unit held together by a suitable clip or wire means, whereby the clip or wire fails upon contact with the molten metal, allowing the components of the additional protective cover to separate and float upwardly. While it may still occur that portions of the slag layer adhere to the outside of the additional protective cover, these same contaminants are carried away from the point of sampling along with the components of the additional protective cover as the latter float upwardly to the surface of the melt.

More particularly, this invention provides a holder for a molten metal sampling device, comprising:

a pipe which is elongated in a given direction, the pipe having an upper portion and a lower portion, the lower portion defining an internal guidance chamber and having an opening lying in a plane making an angle with respect to said given direction, the opening communicating with the guidance chamber, the upper portion being adapted to receive and retain the molten metal sampling device in such a way that molten metal in the guidance chamber can be sampled by the sampling device, a closure element for said opening, the closure element having a density such that it will seek to float upwardly in molten metal outside the pipe, and a protective cover enclosing said closure element and a lower part of said pipe, the protective cover having at least two separate parts, and retaining means for holding the separate parts of the protective cover together around the closure element and the lower part of the pipe, the retaining means being adapted to fail upon contact with the molten metal.

GENERAL DESCRIPTION OF THE DRAWINGS

One embodiment of this invention is illustrated in the accompanying drawings, in which like numerals denote like parts throughout the several views, and in which.

DETAILED DESCRIPTION OF THE DRAWINGS

Figure 1:
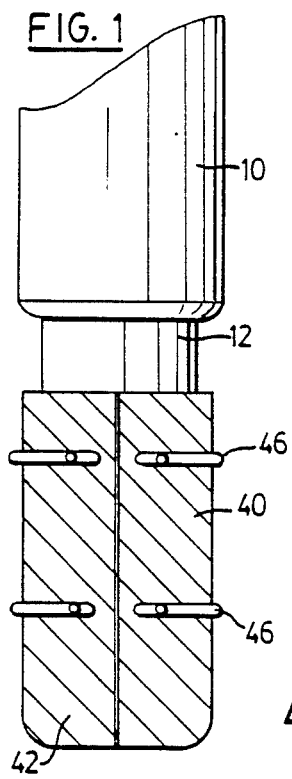
FIG. 1 is an elevational view of a sampler apparatus constructed in accordance with this invention.
Figure 2:
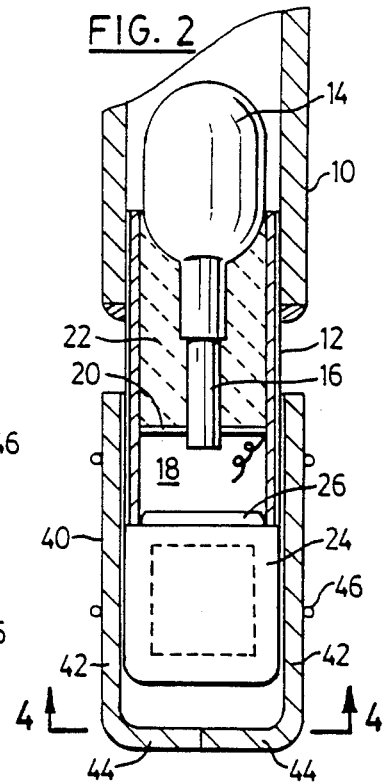
FIG. 2 is an axial sectional view through the apparatus of FIG. 1.
Figure 3:
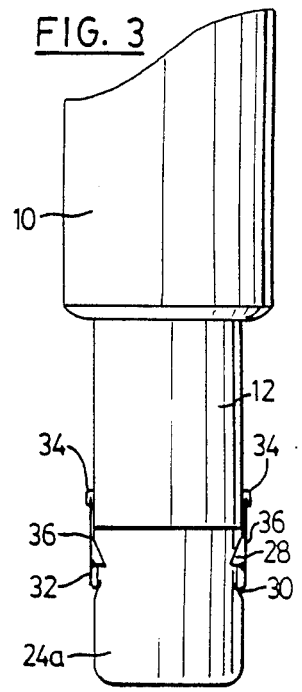
FIG. 3 is an elevational view of the apparatus of FIG. 1 with the outside protective cover removed.

Attention is first directed to FIGS. 1, 2 and 3, which show an external cardboard cylinder 10 with an open bottom end into which partly projects an internal pipe 12 which may be made of alumino silicate reinforced with fiberglass tape. Alternatively, the pipe 12 may be made of Mullite ($3Al_2O_3.2SiO_2$) coated with a Boron Nitride Lubricoat, to discourage liquid slag from adhering to the Tube. The pipe 12 is square-cut at both ends. Within the upper end is lodged a "lollipop"-shaped sampler 14 of known construction which communicates with a tube 16 which is open at the bottom to allow molten metal to enter the sampler 14 after it has entered a chamber 18 lying within the pipe 12 but below a partition 20. Between the partition 20 and the upper end of the internal pipe 12 is provided refractory material 22 or the equivalent, which has the effect of securing the sampler 14 in place. The open bottom end of the pipe 12 is closed by a cap 24 which may be of alumino silicate reinforced with fiberglass tape. Alternatively, the cap 24 may be made of Mullite ($3Al_2O_3.2SiO_2$) coated with Boron Nitride. This item may be either solid or hollow (the hollowness is shown by the broken lines in FIG. 2), and includes an upward protuberance 26 which registers within the open bottom end of the inner pipe 12.

FIG. 3 shows a slightly different configuration for the cap, indicated at 24a. The cap 24a includes two surrounding grooves at 28 and 30, which between them define an outwardly projecting flange 32. Small eyelets 34 at opposite sides of the inner pipe 12 (FIG. 3) each secure one end of a wire 36 which engages a suitable opening in the flange 32. Shortly after the cap 24a contacts the molten metal, the wires 36 fail by melting, allowing the cap 24a to float freely away, thus allowing molten metal into the chamber 18 (FIG. 2). It is to be understood that the cap 24 in FIG. 2 would be secured by some analogous method to that described with respect to FIG. 3.

As an alternative to the use of wires 36 shown in FIG. 3, it is possible to employ fiberglass tape approximately one inch wide to join an seal the parts together. It has been found that the use of tape is less expensive than the use of wires, and functions quite satisfactorily.

Figure 5:
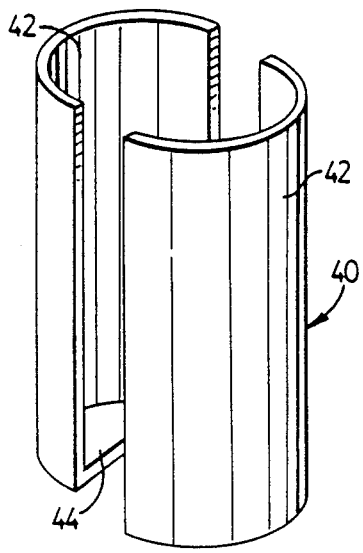
FIG. 5 is a perspective view of one component of this invention.

In FIG. 1 there is shown an outer protective cover 40 which is seen in FIG. 5 to include two geometrically similar, semi-cylindrical side wall portions 42, each with a semi-circular bottom wall 44 (only one visible in FIG. 5). The two-part protective cover 40 is adapted snugly to surround the cap 24 and a lower portion of the inner pipe 12. The two portions of the outer protective cover 40 are shown to be held in place (in the embodiment illustrated) by two spring clips 46.

Figure 4:
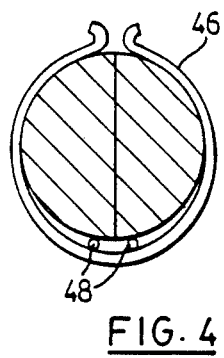
FIG. 4 is a cross-sectional view taken at the line 4—4 in FIG. 2.

Preferably, as shown in FIG. 4, each clip 46 is held in spaced relation away from the outer surface of the protective cover 40 by a pair of protuberances 48. This allows the melt to fully surround at least a portion of each spring clip 46, thus melting the clip more readily upon entry into the melt, whereby the two halves of the outer protective cover 40 spread apart and drift up to the surface of the melt.

It has been found that the provision of the outer protective cover 40 virtually eliminates the risk that slag components will remain close to the bottom of the pipe 12 during the taking of the sample.

In one embodiment, the two-part outer protective cover 40 may be made of alumino silicate reinforced with fiberglass tape. Alternatively, these parts may be made of Mullite coated with Boron Nitride. On the basis of trials for testing purposes, it is believed that the alumina silicate tends to repel contaminants and to discourage the sticking of slag components to its outer surface.

While one embodiment of this invention has been illustrated in the accompanying drawings and described hereinabove, it will be evident to those skilled in the art that changes and modifications may be made therein without departing from the essence of this invention, as set forth in the appended claims The embodiments of the invention in which an exclusive property or privilege is claimed are defined as follows:

1. A holder for a molten metal sampling device, comprising:
    a pipe which is elongated in a given direction, the pipe having an upper portion and a lower portion, the lower portion defining an internal guidance chamber and having an opening lying in a plane making an angle with respect to said given direction, the opening communicating with the guidance chamber, the upper portion being adapted to receive and retain the molten metal sampling device in such a way that molten metal in the guidance chamber can be sampled by the sampling device,
    a closure element for said opening, the closure element having a density such that it will seek to float upwardly in molten metal outside the pipe,
    and a protective cover enclosing said closure element and a lower part of said pipe, the protective cover having at least two separate parts,
    and retaining means for holding the separate parts of the protective cover together around the closure element and the lower part of the pipe, the retaining means being adapted to fail upon contact with the molten metal.

2. The holder claimed in claim 1, in which said protective cover comprises two geometrically similar halves constituting said parts.

3. The holder claimed in claim 1, in which said pipe and said closure element are both cylindrical, are coaxial and have substantially the same diameters, and in which the protective cover comprises two geometrically similar halves constituting said parts, each half having a semi-cylindrical side wall and a semi-circular bottom wall.

4. The holder claimed in claim 3, in which said retaining means is constituted by a metallic element at least partly surrounding the protective cover, the metallic element having at least one location where it is held spaced away from the protective cover, whereby the metallic element will fail by melting at said at least one location.

5. The holder claimed in claim 4, in which the closure element is held against said opening by a further retaining means which is adapted to fail upon contact with the molten metal.

6. The holder claimed in claim 5, in which said further retaining means is a further metallic element, said further metallic element having at least one location where it is held spaced away from the closure element, whereby said further metallic element will fail by melting at said at least one location.

7. The holder claimed in claim 6, in which said plane is substantially perpendicular to the common axis of the pipe and the closure element.

8. The holder claimed in claim 1, in which said plane is substantially perpendicular to said given direction.

* * * * *